United States Patent

Mukouyama et al.

Patent Number: 5,962,280
Date of Patent: Oct. 5, 1999

[54] MICROORGANISMS IMMOBILIZED ON A SOLID SUPPORT WITH A QUATERNARY POLYALLYLAMINE POLYMER

[75] Inventors: Masaharu Mukouyama; Satomi Komatsuzaki, both of Ibaraki, Japan; Koichi Sakano, Frankfurt am Main, Germany

[73] Assignee: Nippon Shokubai Co., Ltd., Osaka, Japan

[21] Appl. No.: 09/022,471

[22] Filed: Feb. 12, 1998

[30] Foreign Application Priority Data

Feb. 14, 1997 [JP] Japan ................................ 9-030647

[51] Int. Cl.$^6$ .............................. C12P 13/20; C12P 7/46; C12N 11/08; C12N 11/04
[52] U.S. Cl. ...................... 435/109; 435/145; 435/177; 435/180; 435/182
[58] Field of Search ..................... 435/174, 177, 435/180, 182, 109, 145

[56] References Cited

U.S. PATENT DOCUMENTS

4,732,851  3/1988  Wood et al. ............................. 435/43

FOREIGN PATENT DOCUMENTS

350714     1/1990   European Pat. Off. .
0 446 948  3/1991   European Pat. Off. .
97/46590   12/1997  WIPO .

Primary Examiner—David M. Naff
Attorney, Agent, or Firm—Foley & Lardner

[57] ABSTRACT

Enzyme-containing cells are immobilized on a water-insoluble support with a polymer represented by the following general formula (I):

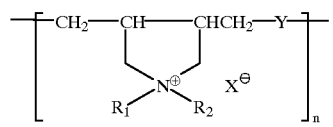

wherein Y is a direct bond or a divalent group represented by the following formula (II)

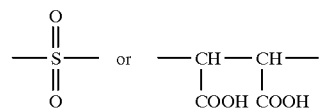

$R_1$ and $R_2$ are each independently hydrogen atoms or organic residues, $X^-$ represents an anion, and n is an integer of 100 to 5000. The support may be in granular form such as granules of ion exchange resins or inorganic carriers, or in sheet form such as ion exchange films or alumina or silica sheets. Immobilization may be carried out by mixing cells with water and a quaternary salt of polyallylamine as the polymer, and sprinkling the resultant mixture onto the solid support and drying. L-aspartic acid or fumaric acid can be produced by contacting fumaric acid and ammonia, or ammonium fumarate, or maleic acid and ammonia, or ammonium maleate, with immobilized cells containing aspartase or maleate isomerase.

8 Claims, No Drawings

MICROORGANISMS IMMOBILIZED ON A SOLID SUPPORT WITH A QUATERNARY POLYALLYLAMINE POLYMER

BACKGROUND OF INVENTION

1. Field of Invention

The present invention relates to a novel immobilized biocatalyst and its use.

2. Related Art

Known immobilized biocatalysts include those wherein enzymes or microorganisms are bound to the surface of a solid support by physical adhesion, ion-bonding or covalent bonding, those wherein enzyme-containing substances, such as cells, are mutually crosslinked, and those wherein enzymes or enzyme-containing substances are covered in a lattice or microcapsules. A different type of immobilized catalyst is described in Japanese Unexamined Patent Publication No. 5-344898, wherein a polyazetidine prepolymer, carboxymethyl cellulose, polyurethane hydrogel prepolymer or polymethylene isocyanate is hardened on the surface of a solid support to immobilize microbial cells on the surface of the support. A disadvantage of these methods, however, is that the enzymes undergo considerable inactivation during the immobilization.

SUMMARY OF INVENTION

It is therefore an object of the present invention to provide a novel immobilized biocatalyst which overcomes this disadvantage.

As a result of much research aimed at overcoming the aforementioned disadvantage, the present inventors completed the present invention upon finding that an immobilized biocatalyst lacking that disadvantage and capable of stably maintaining its enzymatic activity for extended periods can be obtained by binding enzyme-containing cells to a solid support using a polyallylamine-based polymer which is water-soluble under acidic conditions but becomes insoluble under alkali conditions.

The present invention therefore provides an immobilized biocatalyst comprising enzyme-containing cells which are immobilized on a water-insoluble solid support by a polymer represented by the following general formula:

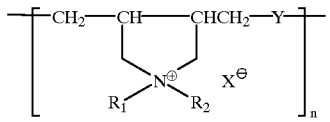

wherein Y is a direct bond or a divalent group represented by the following formula

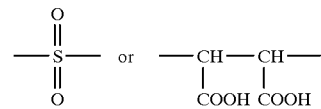

$R_1$ and $R_2$ are each independently hydrogen atoms or organic residues, $X^-$ represents an anion, and n is an integer of 100 to 5000.

The present invention further provides a process for producing L-aspartic acid which is characterized by contacting fumaric acid with ammonia or ammonium fumarate, or maleic acid with ammonia or ammonium maleate on an immobilized biocatalyst which employs cells containing aspartase and/or maleate isomerase, or a combination of such cells, as the above-mentioned cells.

DETAILED DESCRIPTION

The support used for the immobilized biocatalyst of the invention may be either in granular or sheet form, with examples of granules including ion-exchange resins, for example the anionic exchange resins such as Ambalite IRA-904, IRA-94S, Ambalist A-26, A-27 (products of Organo, KK.), and the cationic exchange resins such as Ambalite 200C, 201B, IRC-50 and IRC-76 (products of Organo, KK.); and inorganic carriers such as molecular sieves, alumina, silica and silica gel. The size of the granules is preferably 0.1 mm to 10 mm, and more preferably 0.3 mm to 3 mm. As sheets there may be used ion-exchange films and alumina or silica sheets. The thickness of sheets used is preferably 0.01 mm to 10 mm, and more preferably 0.1 mm to 5 mm.

According to the invention, the resin used for immobilization of the cells is a polymer represented by the following general formula:

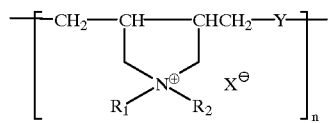

wherein Y is a direct bond or a divalent group represented by the following formula

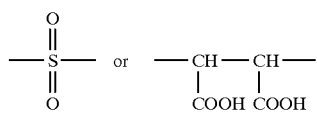

$R_1$ and $R_2$ are each independently hydrogen atoms or organic residues, $X^-$ represents an anion, and n is an integer of 100 to 5000.

When $R_1$ and $R_2$ in the formula are organic residues, they may be alkyl groups of 10 carbon atoms or less such as methyl, ethyl, n-propyl, isopropyl, n-butyl, isobutyl and tert-butyl, among which methyl is particularly preferred. There may also be used halogen- or hydroxyl-substituted organic residues such as 4-chloro-2-dimethylpentyl, 3-ethyl-2,5-dichloroheptyl and 2-hydroxy-3,5-dimethylnonyl, although 3-chloro-2-hydroxypropyl is particularly preferred.

$X^-$ may be a halogen ion such as $F^-$, $Cl^-$, $Br^-$ or $I^-$, among which $Cl^-$ is preferred. Other monovalent anions such as $NO_3-$ and the like may also be used. The number represented by n is preferably 100 to 5000. Specific polymers which may be mentioned include those represented by the following structural formulas.

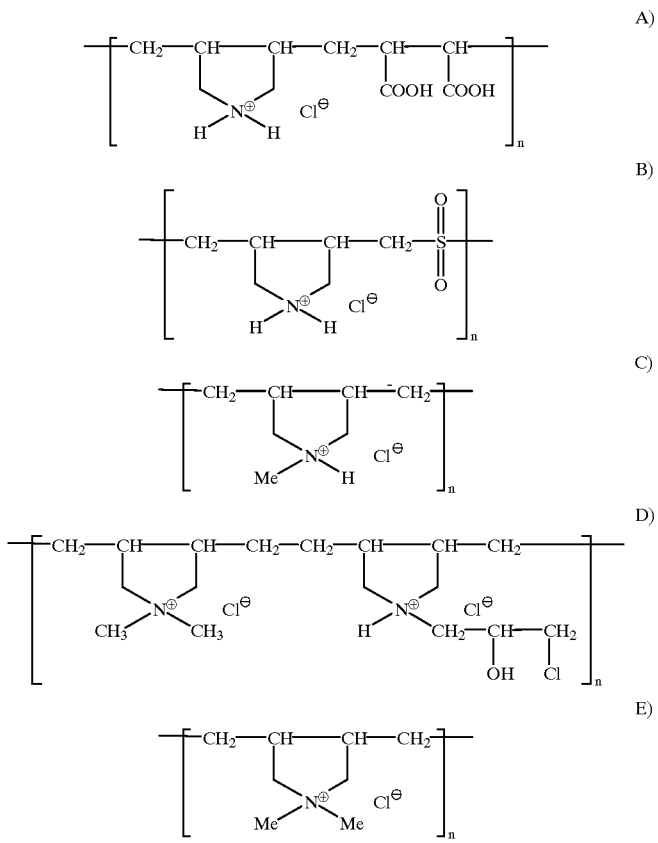

An example of a polymer of formula (A) is PAS410 (tradename), an example of a polymer of formula (B) is PAS92 (tradename), an example of a polymer of formula (C) is PAS-M-1 (tradename), an example of a polymer of formula (D) is PAS-880 and an example of a polymer of formula (E) is PAS-H-5L, all of which may be obtained from Nitto Spinning, KK. Alternatively, for example, the polymer of formula (A) may be produced by 1:1 copolymerization of a diallylamine salt (e.g. a hydrochloride) and maleic acid, the polymer of formula (B) may be produced by copolymerization or radical polymerization of a diallylamine salt (e.g. a hydrochloride) and sulfur dioxide gas, and the polymer of formula (C) may be produced by copolymerization or radical polymerization of diallylmonoalkylamines.

The cells used for the invention may be any cells containing the desired enzyme, including for example, microbial cells such as bacteria, yeast, algae and filamentous fungi, and plant cells. The enzyme is not particularly restricted, and examples of various enzymes include aspartase which converts ammonium fumarate into L-aspartic acid, maleate isomerase which converts maleic acid into fumaric acid, fumarase which converts fumaric acid into L-malic acid, malease which converts maleic acid into D-malic acid, and hydratase which converts cis-epoxysuccinic acid into L-tartaric acid. More specific examples of cells which may be used are bacterial cells containing aspartase, bacterial cells containing maleate isomerase, and bacterial cells containing both aspartase and maleate isomerase.

The following are more specific examples of microbial cells which may be used.

TABLE 1

Types of reactions using immobilized biocatalysts

| Starting material | Product | Enzyme | Cells |
|---|---|---|---|
| Ammonium fumarate | L-aspartic acid | aspartase | *Escherichia coli* ATCC 11303 |
| | | | *Escherichia coli* ATCC 9637 |
| | | | *Escherichia coli* ATCC 27325 |
| | | | Brevibacterium |
| Maleic acid | fumaric acid | maleate isomerase | Pseudomonas |
| | | | *Pseudomonas maltophilia* ATCC 13270 |
| Ammonium maleate | L-aspartic acid | maleate isomerase + aspartase | Alcaligenes |
| | | | *Alcaligenes faecalis* ATCC 8750 |
| | | | Also, combinations of microbes with maleate isomerase activity and microbes with |

TABLE 1-continued

Types of reactions using immobilized biocatalysts

| Starting material | Product | Enzyme | Cells |
|---|---|---|---|
| Fumaric acid | L-malic acid | fumarase | aspartase activity<br>Microbes with aspartase activity<br>*Escherichia coli* IEO 3301<br>*Bacillus stearothermophilus* DSM 2234<br>*Sulfolobus solfataricus* ATCC 49255 |
| Maleic acid | D-malic acid | malease | *Pseudomonas pseudoalcaligenes* NSM-5<br>NSM-6<br>FERM P-15561<br>P-15562 |
| Cis-epoxy-succinic acid | L-tartaric acid | hydratase | *Acinetobacter tartarogenes* ATCC 31105 |

When a polymer represented by the above general formula (4) is added at low concentration to a culture solution obtained by culturing one of these microbes, the cultured cells can be condensed and precipitated, thus simplifying the procedure since centrifugation of a large amount of the culture solution is unnecessary.

Specifically, the polymer represented by the above general formula (4) is added to a culture solution of the microbes to be immobilized to a solid content of 10–10,000 ppm, and preferably 100–1000 ppm, and after being allowed to stand the microbial cells aggregate and precipitate. Cooling the culture solution in advance is effective for preventing reduction of the desired enzyme activity.

After thus precipitating the microbial cells, the supernatant may be drawn out to reduce the liquid amount by a few times. For example, after 500 ppm of PAS-880 has been added to 1 L of culture solution and allowed to stand for 30 minutes, approximately 800 ml may be separated off as the supernatant. The remaining cell aggregate can then be subjected to low-speed centrifugation at 3000 rpm to recover the cells as a cake.

Because the aggregated cells can be sufficiently separated even with a low-speed centrifuge, it is possible to recover the cells with simple equipment.

The recovered cells may then be mixed with the pH-adjusted polymer either directly or after addition of water, and used as the immobilized material.

In immobilization of the cells, either one type of cell may be immobilized or two or more different types of cells may be immobilized. For example, bacterial cells containing maleate isomerase and bacterial cells containing aspartase may be immobilized in combination.

The cell immobilization may be accomplished by first mixing the cells with water and a neutral to weakly basic liquid polymer, and sprinkling it onto the solid support and drying it. The drying may be carried out using a common particle drier capable of not inactivating the enzyme in the cells, such as a rotary evaporator, fluidized bed drier or spray drier.

When the amount of immobilized cells is insufficient after a single operation, the sprinkling operation and drying operation of the polymer/cell mixture on the solid support may be repeated a number of times, for example 2 to 5 times. The proportion of the cells to be immobilized and the polymer is 4 to 200 kg, and preferably 10 to 50 kg, of polymer per 1 kg of cells (dry weight). When preparing a mixture of the polymer and cells, the amount of water added is 5 to 400 kg, and preferably 20 to 100 kg, per 1 kg of the cells. The thickness of the polymer layer containing the immobilized cells is 0.01 to 0.3 mm, and preferably 0.1 to 0.2 mm.

If the immobilized catalyst is in the form of a film, the above-mentioned cell/polymer mixture may be applied onto a sheet-like support and then dried. The density of the immobilized cells may be adjusted by varying the amount of application or the number of times the application/drying cycle is repeated.

One exemplified application for an immobilized biocatalyst of the invention is production of L-aspartic acid. In this case, an immobilized biocatalyst with immobilized aspartase-containing cells, especially bacterial cells, is packed into a column and an aqueous solution of fumaric acid and ammonia or an aqueous solution of ammonium fumarate is passed through the column.

Alternatively, an immobilized biocatalyst with immobilized cells (for example, bacterial cells) containing aspartase and maleate isomerase, or an immobilized catalyst with both immobilized cells containing aspartase and cells containing maleate isomerase on a single immobilizing support, is packed into a column and an aqueous solution of maleic acid and ammonia or an aqueous solution of ammonium maleate is passed through the column, to produce L-aspartic acid by a single-step process from maleic acid.

Still alternatively, both an immobilized biocatalyst with immobilized cells containing maleate isomerase and an immobilized catalyst with immobilized cells containing aspartase are combined and packed into a column and an aqueous solution of maleic acid and ammonia or an aqueous solution of ammonium maleate is passed through the column, to produce L-aspartic acid by a single-step process from maleic acid.

Still alternatively, an immobilized biocatalyst with immobilized cells containing maleate isomerase and an immobilized catalyst with immobilized cells containing aspartase are packed into separate columns, and an aqueous solution of maleic acid and ammonia or an aqueous solution of ammonium maleate is first passed through the immobilized biocatalyst with immobilized maleate isomerase to convert the maleic acid to fumaric acid, and is then passed through the column of the immobilized biocatalyst with immobilized aspartase to convert the ammonium fumarate to L-aspartic acid.

EXAMPLES

The present invention will now be explained in more detail by way of examples, although the invention is in no way to be limited thereby. The reaction products were analyzed by liquid chromatography.

Example 1

A 5 L jar fermenter was loaded with 3 L of medium (pH 6.3) comprising a composition of 10 g of fumaric acid, 5 g of $(NH_4)_2SO_4$, 1 g of $KH_2PO_4$, 3 g of $K_2HPO_4$, 0.5 g of $MgSO_4.7H_2O$, 5.5 g of NaOH and 20 g of yeast extract in 1 L of distilled water, and *Escherichia coli* ATCC 11303 was inoculated thereto for aeration agitation culturing at 37° C. Culturing was continued for twenty hours, and the cells were collected by centrifugation.

After preparing a mixture of 70 g of PAS-880 (product of Nitto Spinning, KK.) with the pH adjusted to near 7 with an alkali and 230 g of deionized water, the above-mentioned cells were dispersed therein. In a 6 L volume eggplant-shaped flask was placed 300 ml of an ion-exchange resin (Ambalite IRA-94S Cl, average particle size: 0.5 mm, product of Organo, KK.) and 20 0.5-inch Teflon spheres, after which ⅙ of the previously obtained cell dispersion was added and subjected to vacuum drying for one hour with an evaporator at 30° C. while rotating, to coat the ion-exchange resin with the cells. After this operation was repeated 6 times, the Teflon spheres were removed to obtain beads of immobilized biocatalyst.

The immobilized biocatalyst as prepared above was immersed overnight in a 20% ammonium fumarate solution (pH 8.5) at 4° C., after which 50 ml thereof was filled into a jacketed column and 30° C. warm water was circulated through the jacket to bring the temperature of the reactor to 30° C.

A substrate solution in a capped bottle (200 g of fumaric acid, 200 g of 25% ammonia water, 0.25 g of $MgSO_4.7H_2O$ and 1 g of sodium sulfite in 1 L, adjusted to pH 8.3 with ammonia) was fed through a Teflon tube and passed through the column at a rate of 25 ml per hour for continuous reaction.

Upon analyzing the, reaction solution in the 6th hour after initiating the reaction, a reaction product i.e., L-aspartase acid was found in a roughly equimolar amount compared to the fumaric acid consumed, with a reaction conversion rate of 99.7%.

The Conversion rate of 99.7% was maintained up to the 7th day, 1st month and even 4th month after initiating the reaction. No change was observed in the form of the immobilized biocatalyst.

Examples 2 to 4

The procedure of Example 1 was repeated using PAS-M-1 (Example 2), PAS-410 (Example 3) and PAS-H-5L (Example 4) as immobilizing polymers instead of PAS-880.

The results are summarized in Table 2.

TABLE 2

| Example | Polymer | Initial conversion rate (%) | Conversion rate after 7 days (%) |
| --- | --- | --- | --- |
| 1 | PAS-880 | 99.7 | 99.7 |
| 2 | PAS-M-1 | 99.8 | 99.7 |
| 3 | PAS-410 | 99.8 | 99.7 |
| 4 | PAS-H-5L | 99.6 | 99.6 |

The conversion rate from fumaric acid to L-aspartic acid did not decrease even after 7 days of use.

Example 5

*Escherichia coli* ATCC 11303 was cultured, in the same manner as Example 1, by aeration/agitation culturing at 37° C. After 20 hours of culturing the medium was cooled to 10° C., 3 g of PAS-880 was added, and after 5 minutes of agitation the mixture was left to stand without agitation. When the cells aggregated and precipitated after 30 minutes, about 2.5 L of the supernatant was drawn out. The remaining solution was then drawn out together with the cells and subjected to low-speed centrifugation to recover 120 g of wet cells.

After preparing a mixture of 70 g of PAS-880 (product of Nitto Spinning, KK.) with the pH adjusted to near 7 with an alkali and 170 g of deionized water, the above-mentioned cells were dispersed therein. In a 6 L volume eggplant-shaped flask were placed 300 ml of an ion-exchange resin (Ambalite IRA-94S Cl, average particle size: 0.5 mm, product of Organo, KK.) and 20 0.5-inch Teflon spheres, after which ⅙ of the previously obtained cell dispersion was added and subjected to vacuum drying for one hour with an evaporator at 30° C. while rotating, to coat the cells with the ion-exchange resin. After this operation was repeated 6 times, the Teflon spheres were removed to obtain beads of an immobilized biocatalyst.

The immobilized biocatalyst as prepared above was immersed overnight in a 20% ammonium fumarate solution (pH 8.5) at 4° C., after which 50 ml thereof was filled into a jacketed column and 30° C. warm water was circulated through the jacket to bring the temperature of the reactor to 30° C.

A substrate solution in a capped bottle (200 g of fumaric acid, 200 g of 25% ammonia water, 0.25 g of $MgSO_4.7H_2O$ and 1 g of sodium sulfite in 1 L, adjusted to pH 8.3 with ammonia) was fed through a Teflon tube and passed through the column at a rate of 25 ml per hour for continuous reaction.

Upon analyzing the reaction solution in the 6th hour after initiating the reaction, a reaction product i.e., L-aspartase acid was found in a roughly equimolar amount with the fumaric acid consumed, with a reaction conversion rate of 99.7%.

The conversion rate of 99.7% was maintained up to the 7th day, 1st month and even 4th month after initiating the reaction. No change was observed in the form of the immobilized biocatalyst.

We claim:

1. An immobilized biocatalyst comprising enzyme-containing cells which are immobilized on a water-insoluble solid support by a polymer represented by the following general formula:

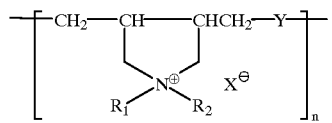

wherein Y is a direct bond or a divalent group represented by the following formula

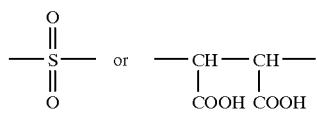

$R_1$ and $R_2$ are each independently hydrogen atoms or organic residues, $X^-$ represents an anion, and n is an integer of 100–5000.

2. The immobilized biocatalyst according to claim 1, wherein said support is an ion-exchange resin or inorganic support.

3. The immobilized biocatalyst according to claim 1, wherein said support comprises granules or a sheet.

4. The immobilized biocatalyst according to claim 1, which comprises bacterial cells containing aspartase and/or maleate isomerase, or a combination of such bacterial cells.

5. The immobilized biocatalyst according to claim 2, wherein said support comprises granules or a sheet.

6. The immobilized biocatalyst according to claim 2, which comprises bacterial cells containing aspartase and/or maleate isomerase, or a combination of such bacterial cells.

7. The immobilized biocatalyst according to claim 3, which comprises bacterial cells containing aspartase and/or maleate isomerase, or a combination of such bacterial cells.

8. A process for producing L-aspartic acid or fumaric acid, comprising contacting fumaric acid and ammonia, or ammonium fumarate, or maleic acid and ammonia, or ammonium maleate, with the immobilized enzyme-containing cells according to claim 4.

* * * * *